United States Patent [19]

Wasik

[11] 4,210,020

[45] Jul. 1, 1980

[54] PASTA TESTING DEVICE

[76] Inventor: Ronald J. Wasik, 2880 E. Cedarwood Dr., Ottawa, Ontario, Canada

[21] Appl. No.: 899,492

[22] Filed: Apr. 24, 1978

[51] Int. Cl.² ............................................ G01N 33/10
[52] U.S. Cl. ........................................ 73/169; D7/102
[58] Field of Search ............... 73/169; 99/342; 350/88; 356/194, 244; D7/105, 102

[56] References Cited

U.S. PATENT DOCUMENTS

| D. 157,874 | 3/1950 | Kolden | D7/105 |
|---|---|---|---|
| 203,068 | 4/1878 | Pekar | 73/169 |
| D. 213,990 | 4/1969 | Lee | D7/105 |
| 2,597,425 | 5/1952 | Aiken et al. | 356/244 X |
| 3,198,064 | 8/1965 | Moore | 356/244 |
| 4,012,068 | 3/1977 | Apodaca | D7/105 X |

FOREIGN PATENT DOCUMENTS

| 597188 | 8/1959 | Italy | 73/169 |
|---|---|---|---|
| 2392 | of 1876 | United Kingdom | 73/169 |

OTHER PUBLICATIONS

Encyclopedia of Food Technology and Food Services, vol. 2, 1974, pp. 558-570.

*Primary Examiner*—Gerald Goldberg
*Assistant Examiner*—Joseph W. Roskos

[57] ABSTRACT

A pasta testing device consisting of a pair of flat elongate transparent plates whose sides stand normal to the flat surfaces and have edges sufficiently clean and sharp to impinge or bite into the softened hydrated surface portion of a strand of pasta to deter the longitudinal movement thereof. At least one of the plates may be colored. The opposite sides of the plates are notched in transversely registering pairs, the notches being preferably of generally rectangular form and disposed vertically relative to the flat surface of the plate and of a size sufficient to accommodate a single strand of pasta. The vertical sides of the plates and the notches have clean sharp edges where they meet the flat surface of the plates. Slide resistance of the notches is further increased when the inner vertical side is provided with an inwardly facing, inverted V-shaped ridge. A single notch near the outer end of a plate is provided for use in extracting a strand of spaghetti from a hot cooking utensil.

6 Claims, 5 Drawing Figures

PASTA TESTING DEVICE

BACKGROUND OF THE INVENTION

This invention relates to improvements in a device for testing pasta appertaining particularly to a device for quickly and easily determining the precise degree of hydration of pasta during the cooking operation.

Over a long period of time pasta foods have been in use in many parts of the world. Mounting interest in the possibility of using pasta as a vehicle for improving nutrition has created a need for a better understanding of the role of the constituents. For this reason, organizations such as the Grain Research Laboratory, Food Research Institute, U.S. Department of Agriculture and the Food and Agriculture Organization of the United Nations have been assessing tests on the chemical, physical and sensory properties of pasta for some years. Therefore there is a recognized need to improve both the nutritional and eating quality of pasta.

The wide acceptability of pasta products for domestic and institutional use depends on several quality factors such as colour, finish and cooking properties, and on cooked pasta texture (eating quality). Of the various kinds or shapes of pasta comprising such forms as vermicilli, spaghetti, macaroni, noodles, etc., spaghetti is considered the preferred test material being considerably more sensitive than macaroni. Spaghetti is also the preferred form of pasta products in North America and Europe.

The importance of proper cooking of pasta has led to various methods of testing the cooked product from sensory to instrumental, e.g. A mercury-loaded plunger was timed to compress a sample and its tenderness score was based on time the weight needed to break the sample. An instrument was marketed to conduct tensile tests on cooked spaghetti. The apparatus was used to measure elasticity flow, rupture and relaxation properties of noodles. A bite test employing a loaded cutting edge with its penetration being recorded electronically has also been used.

Statistics show primary consumer reaction is based on shearing resistance perceived on the first bite and since scientific research has shown that shearing resistance is related to the extend to which the pasta has been cooked (or hydrated), it is very important to know and be able to measure the cooking time or that time it takes for pasta to hydrate in boiling water especially if one wishes to have reproducible results. Studies have also shown that the cooking rate of pasta may be followed with great precision using the "Braibanti" technique.

The optimum cooking time according to the "Braibanti" technique calls for extracting a strand of pasta as the cooking progresses and squeezing the same between two flat transparent plates hinged together at one edge and regarding the compressed core. As the spaghetti approaches the optimum cooking time, a thin white line representing the core of the slick running down the centre of the flattened mass indicates moisture pentration and that the starch, except in this core, is partially or completely gelatinized. (It is assumed that this simulates the common squeeze test used in cooking by the consumer.) For this purpose, "Braibanti Pincers" have long been available but certain deficiencies have negated their general adoption; namely the difficulty of extracting a strand of hot, partly cooked spaghetti from the cooking utensil and placing it transversely on the lower plate, the inclination of the strand to slip longitudinally off the side of the plate and the tendency of the soft slippery strand to slide along the plate and off the end as the hinged plates are closed.

OBJECTS OF THE INVENTION

It is an object of this invention to provide a simple pasta testing device comprising a pair of hinged transparent plates that will deter the longitudinal sliding of a strand of spaghetti placed thereon.

A further object is to provide a pasta testing device that will inhibit the movement of a strand of pasta out of the device on the squeezing of the pair of plates.

A further object is to provide a testing device that may be used to extract a single strand of spaghetti from a hot cooking utensil.

A still further object of the invention is the provision of a pasta testing device of the nature and for the purpose described that is characterized by structural simplicity, ease of operation and low cost of production whereby the same is rendered commercially desirable.

BRIEF DESCRIPTION OF THE DRAWINGS

To the accomplishment of these and related objects as shall become apparent as the description proceeds, the invention resides in the construction, combination and arrrangement of parts as shall be herein after more fully described, illustrated in the accompanying drawings and pointed out in the claims hereunto appended.

IN THE DRAWINGS

Figure 1:
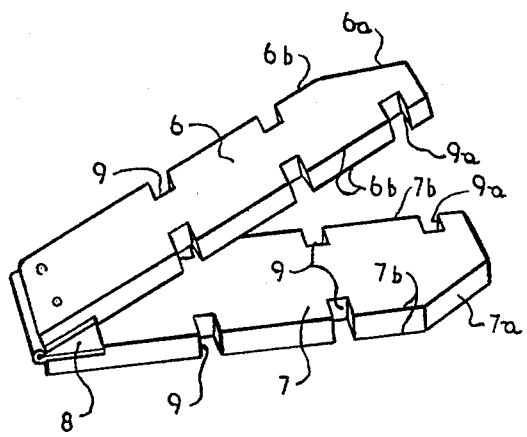
Figure 2:
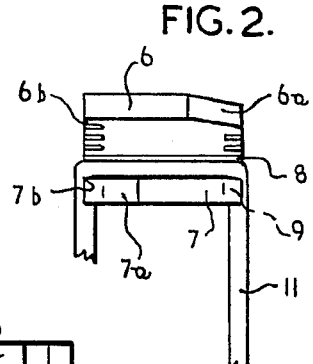
Figure 3:
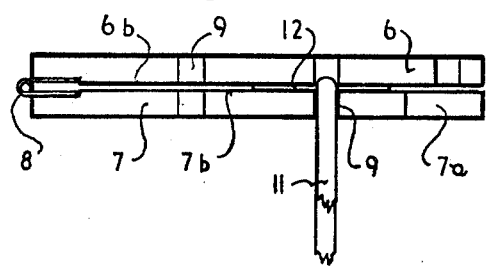
Figure 4:
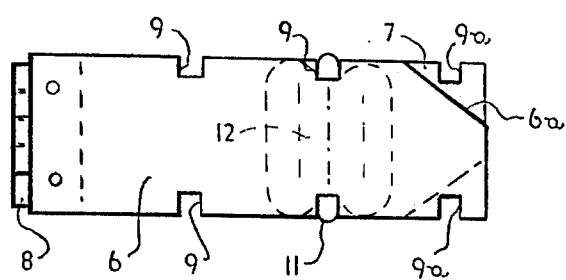

FIG. 1 is an isometric view of the pasta testing device;

FIG. 2 is a front elevation of device;

FIG. 3 is a side elevation thereof;

FIG. 4 is a plan view; and

Figure 5:
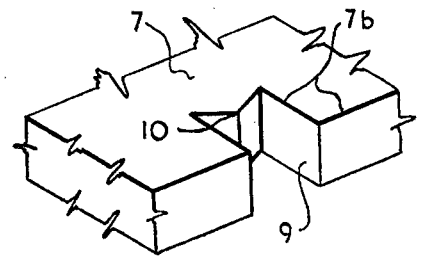

FIG. 5 is an enlarged isometric view of one of the side notches.

DETAILED DESCRIPTION OF THE INVENTION

Referring now particularly to the drawings this pasta testing device will be seen to comprise a pair of separable, flat, elongate, transparent plates 6 and 7 approximately 3.0×8.0×0.3 cm thick connected at one end by a hinge 8 to allow confronting surfaces of the plate to have uniform contact when closed. At their free ends each plate of this pair of pincer plates has a corner cut away at an angle as at 6a and 7a respectively on opposite sides to facilitate separation of the plates as when stuck together with pasta. In this form the device is invertable, either plate may be in upper or lower position.

In employing the Braibanti technique in the past, a common complaint has been the difficulty in preventing a strand of spaghetti about to be tested from slipping longitudinally. Accordingly the opposite sides of plates 6 and 7 are arranged to stand normal, i.e. at right angles to the flat surface and have clean sharp edges 6b and 7b respectively along such sides to impinge or bite into the slippery, softened hydrate surface of a transversely disposed strand of spaghetti where it bends over the opposite edges of the plate, to deter or restrain the longitudinal movement of the pasta strand.

A further problem in testing a strand of cooked spaghetti is the tendency of the soft, slippery strand to move out toward the open end of the pincer plates as they are being closed. Attempts have been made to provide slippage resistance by roughening or transversely ridging the confronting faces of the plates but with poor and unsatisfactory results. In this invention, notches 9 are provided along opposite sides of the plates in transversely registering pairs—actually a single notch on opposite sides of the lower plate arranged in transverse registry could suffice. Such a pair of notches 9 will provide accommodating seats for the depending reaches of a tansversely disposed strand of spaghetti that hang down from opposite sides of the plate, as seen particularly in FIGS. 2, 3 and 4. The preferred notch 9 is of generally rectangular form, disposed vertically relative to the flat surface of the plate and of a size sufficient to accommodate a single pasta strand. Semi-circular and V-shaped notches proved unacceptable in that they provided less sliding resistance than the rectangular ones. The rectangular shaped notch 9 gained increased slide resistance when the inner vertical side was provided with an inwardly facing, inverted V-shaped ridge 10, as shown clearly in the enlarged isometric detail of FIG. 5. In all cases the vertical sides of the plates—and the notches—have the clean sharp edges 6b and 7b where they meet the flat surface of the plates as previously mentioned.

In FIGS. 2, 3 and 4 a single strand of spaghetti 11 is seen extending transversely of the lower plate 7 with its opposite end reaches depending from a transversely registering pair of notches 9. In FIGS. 2 and 3 where the upper plate 6 has been closed, the cooked hydrate reach of pasta between the pincer plate has been pressed flat as shown at 12 when the precise degree of cooking is clearly seen. Some like the hard cooked "al dente" pasta when a thin line of ungelatinized core can be detached while optimum cooking is attained where a faint resemblance of ungelatinized starch has just been eliminate from the center line extending across the pressed test sample.

Preferred material for the flat transparent plates of this device are glass, vinyl, polycarbonate, "Lexan", "Plexiglass" or the like. I have found it is easier to read the sample being tested when at least one plate is coloured or tinted, the best colours being pale yellow, red, grey or bronze, to emphasize the gelatinized condition of the specimen.

In its present form, where each of the pincer plates 6 and 7 has a cut off corner at its outer end, I never—the—less provide a single notch 9a on the full side for the special task of extracting a single strand of spaghetti from a hot cooking utensil. Normally this is done with a fork, a pair of tweezers, or some other extraneous item but with these specially located slip-resistant notches 9a this device meets this additional need.

As already mentioned the separable plates 6 and 7 are here shown as connected at one end by a hinge 8 but in some circumstances it may be found desirable to provide (a) a pair of unattached plates that can be pressed together by hand or test machine—or (b) the plates may be formed integral in a U-shaped design with a relatively flexible connecting part—or—(c) two individual plates may be conveniently held together as by a common ring.

It must be understood that pastas prepared from the same or different varieties of wheat by the same or different manufactures may vary considerably in cooking time. Variables that can contribute to cooking time differentials include particles size, protein content, moisture content at extrusion, rate and type of drying and moisture content of the finished raw product.

Where this device is employed for precise comparative testing of pasta products, it is essential that similar size and shape sections of the product, be it macaroni, noodles, or fancy shaped items, be presented.

In testing, when samples of pasta are pressed between two transparent plates and subjected to microscopic examination under polarized lights at 10× and 40× magnification, different areas or zones of cooking may be revealed. Starch from partially cooked samples revealed almost no less of birefringence, suggesting that virtually no gelatinization had taken place during soaking. While high-protein samples showed three zones and low-protein samples only two, the outer zone for all samples showed almost total loss of birefringence while the inner core showed very little gelatinization. The middle zone of the high-protein showed intermediate loss of birefringence. After the samples had been cooked to "al dente", loss of birefringence was almost total and no separate zones of cooking could be detected. It was further found that when using Tunisian durum, the high-protein sample took 1.5 minutes longer to cook than the low-protein sample whereas samples of pasta made from Leeds durum required the same cooking time to reach "al dente" regardless of the protein content. All of this emphasized to need and importance of employing the Braibanti technique in constantly monitoring optimum cooking time for spaghetti.

From the foregoing description it will be apparent that an improved pasta testing device is provided that will fulfill all the requirements thereof but it is to be understood that changes can be made thereto that do not depart from the spirit or scope of the appended claims.

I claim as my invention:

1. A pasta testing device comprising a pair of flat elongate transparent plates wherein opposite sides of said plates stand normal to the flat surfaces and have edges that are sufficiently clean and sharp to impinge the softened hydrated surface of a transversely disposed strand of pasta to deter the longitudinal movement of such strand and wherein the sides of said plates are notched to provide accommodating seats for the depending and reaches of a transversely disposed strand of softened hydrated pasta to deter the unwanted sliding of the strand longitudinally off the plates.

2. The device according to claim 1 wherein at least one of said plates has a notch on each of opposite longitudinal sides arranged in a transversely registering pair.

3. The device according to claim 2 wherein each notch is disposed vertically relative to the flat surface of the plate and is of a size sufficient to accommodate the depending end reaches of a single strand of pasta.

4. The device according to claim 1 wherein each notch is of generally rectangular form.

5. The device according to claim 4 wherein each vertically disposed rectangular notch has an inwardly facing, inverted V-shaped ridge in the base thereof which ridge may impinge the depending end reach of a softened hydrated pasta strand.

6. The device according to claim 1 wherein one of said plates has a notch near its outer end to accommodate a single strand of pasta in extracting the same from a hot cooking utensil.

* * * * *